(12) United States Patent
Daiss et al.

(10) Patent No.: US 8,692,012 B2
(45) Date of Patent: Apr. 8, 2014

(54) METHOD FOR PRODUCING ESTER-FUNCTIONAL SILANES

(75) Inventors: Juergen Oliver Daiss, Munich (DE); Juergen Stohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/580,358

(22) PCT Filed: Feb. 9, 2011

(86) PCT No.: PCT/EP2011/051890
§ 371 (c)(1),
(2), (4) Date: Nov. 2, 2012

(87) PCT Pub. No.: WO2011/101278
PCT Pub. Date: Aug. 25, 2011

(65) Prior Publication Data
US 2013/0060057 A1    Mar. 7, 2013

(30) Foreign Application Priority Data

Feb. 22, 2010  (DE) .......................... 10 2010 002 202

(51) Int. Cl.
*C07F 7/04*    (2006.01)
(52) U.S. Cl.
USPC ........................................ 556/440
(58) Field of Classification Search
USPC ........................................ 556/440
See application file for complete search history.

(56) References Cited

U.S. PATENT DOCUMENTS

2008/0293958 A1    11/2008  Bauer et al.

FOREIGN PATENT DOCUMENTS

| JP | 2200689 A | 8/1990 |
| JP | 2005-314246 A | 11/2005 |
| WO | 2005/103061 A1 | 11/2005 |
| WO | 2005103061 A1 | 11/2005 |
| WO | 2007/063011 A1 | 6/2007 |

OTHER PUBLICATIONS

Stefan Altmann et al., "The Hydrolysis/Condensation Behaviour of Methacryloyloxyalkylfunctional Alkoxysilanes: Structure-Reactivity Relations", Monatshefte fur Chemie, vol. 134, (2003) pp. 1081-1092.
B.P. Whim, and P.G. Johnson (editors), "Directory of Solvents", First Edition 1996, Blackie Academic & Professional (Chapman & Hall, London, Weinhelm, New York, Tokyo, Melbourne, Madras), ISBN 0 7514-0245-1.

*Primary Examiner* — Johann R Richter
*Assistant Examiner* — Kofi Adzamli
(74) *Attorney, Agent, or Firm* — Brooks Kushman P.C.

(57) ABSTRACT

Silanes containing an ester group are produced in high yield and purity by reacting a salt of a carboxylic acid with a silane containing a carboxylate substitutable leaving group following by distilling the product mixture to obtain a distillate containing the ester group containing silane product, wherein a solvent having a boiling point higher than the product is contained in the product mixture during at least a terminal portion of the distillation.

11 Claims, No Drawings

METHOD FOR PRODUCING ESTER-FUNCTIONAL SILANES

CROSS-REFERENCE TO RELATED APPLICATIONS

This application is the U.S. national phase of PCT Appln. No. PCT/EP2011/051890 filed Feb. 9, 2011, which claims priority to German Patent Application No. 10 2010 002 202.0 filed Feb. 22, 2010, which are incorporated herein by reference.

BACKGROUND OF THE INVENTION

1. Field of the Invention

The present invention relates to processes for producing silanes having an ester group with a silicon atom in the alcohol-derived portion of the ester.

2. Description of the Related Art

Ester-functional silanes having a silicon atom in the alcohol-derived portion of the ester can be represented by the formula I, which also illustrates which portion of the ester is referred to as the "alcohol-derived portion" and which is referred to as the "carboxylic acid-derived portion":

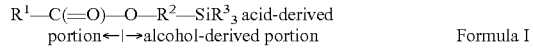

When none of the $R^3$ radicals is hydrolyzable, the esters are obtainable by reacting an alcohol of the structure $HO\text{---}R^2\text{---}SiR^3_3$ with a carboxylic acid of the structure $R^1\text{---}C(=O)\text{---}OH$ or with derivatives thereof (e.g., ester, acid anhydride, acid azide; general structure: $R^2\text{---}C(=O)\text{---}Y$; $\text{---}Y=\text{---}OH$, $\text{---}O$-alkyl, $\text{---}O$-aryl, $\text{---}O$-acyl, $\text{---}N_3$, $\text{---}Cl$ etc):

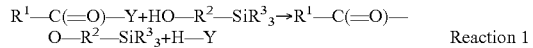

H—Y can be trapped with an auxiliary base, if necessary. When at least one of the $R^3$ radicals is hydrolyzable, an alcohol of the structure $HO\text{---}R^2\text{---}SiR^3_3$ will condense with itself by eliminating one $H\text{---}R^3$ equivalent to form a silaoxacycle or its oligomer. The reaction pathway depicted in reaction 1 is therefore regrettably not applicable to such silanes.

Alternatively, some of these ester-functional silanes are obtainable by attaching an ester of the structure $R^1\text{---}C(=O)\text{---}O\text{---}CH=CH_2$ or of the structure $R^1\text{---}C(=O)\text{---}O\text{---}R'\text{---}CH=CH_2$ by hydrosilylation to a silane which has at least one Si—H bond (reaction 2). However, this method is restricted to ester-functional silanes with at least two carbon atoms between the silicon atom and the ester function; hydrosilylation frequently shows poor regioselectivity at the double bond; and hydrosilylation catalysts frequently also catalyze cleavage of the C(O)O—C bond as a simultaneous reaction, especially when allyl esters are involved.

The third usable type of reaction for preparing such silanes involves a salt of a carboxylic acid, i.e., a carboxylate, being reacted with a silane having an Si-attached hydrocarbon group with a leaving group "X":

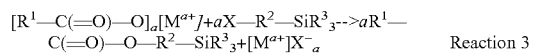

This reaction pathway does not have the disadvantages of the first two pathways. For instance, it is also applicable to silanes having hydrolyzable radicals $R^3$ or only one carbon atom in $R^2$. As will be apparent, however, the salt $[M^{a+}]X^-_a$ is formed along this route. An aqueous workup to remove the salt is only possible if the product is not hydrolysis-sensitive, which however will be generally the case if the silanes thus obtained are to be sufficiently reactive at one or more of the $R^3$ groups to permit using the silanes for producing organofunctional silicones or for moist crosslinking. Nonaqueous removal of the salt requires a centrifugation or filtration step. Such methods are described for example in WO 2007 063 011 or in Monatshefte für Chemie, 2003, volume 134, pp. 1081-1092. The salt has to be washed at some cost and inconvenience, yet product residues frequently remain in the salt despite washing and are lost in this way. After filtration, the filtrate can be subjected to a fractional distillation. If the filtration step were omitted and the distillation were to be carried out directly in the presence of the salt, the salt would increasingly dry out in the distillation pot during the distillation and become encrusted therein, the commixing and hence the separation efficiency of the distillation would become increasingly worse, frequently leading to local overheating and hence to the risk of exothermic decomposition reactions being triggered. The salt bakes onto the distillation pot during the distillation and is very difficult to remove thereafter. Furthermore, unconverted carboxylate can trigger undesired side-reactions in a distillation without a prior filtration if $R^1$, $R^2$ or $R^3$ contain sensitive groups. If a solvent were to be used in the reaction or to wash the salt, the solvent first has to be time-consumingly distilled off before the product can be recovered. It would be desirable to have a process that permits distillation directly in the presence of the salt without any filtration step, ideally without product being lost as the result of silane of formula I adhering to the salt (as is generally the case with a filtration) or that avoids the laborious distillative removal of the solvent prior to the actual product distillation, or ideally both.

SUMMARY OF THE INVENTION

The invention provides a process for producing silanes of general formula I

by reacting at least one salt of a carboxylic acid of general formula II

with at least one silane of general formula III

wherein said process includes at least one distillative step wherein the distillate contains at least one silane of general formula I, and wherein at least one high-boiling solvent HBS is present,
wherein HBS, when measured at the pressure at which the distillative step is carried out, has a higher boiling point than the silane of general formula I, and wherein
X is a leaving group which is carboxylate substitutable,
$R^1$ is a monovalent $C_1$-$C_{18}$ hydrocarbon radical which is unsubstituted or substituted with one or more groups Q and which may be interrupted by one or more heteroatoms, or is a hydrogen atom,
$R^2$ is a divalent $C_1$-$C_{18}$ hydrocarbon group which is unsubstituted or substituted with one or more groups Q and which may be interrupted by one or more heteroatoms,
$R^3$ is hydrogen, an unsubstituted or Q-mono- or -polysubstituted monovalent $C_1$-$C_{18}$ hydrocarbon group, $C_1$-$C_{18}$ hydrocarbonoxy group, $Si_1$-$Si_4$ silane group or an $Si_1$-$Si_4$ siloxy group which may be interrupted by one or more heteroatoms,
$M^{a+}$ is an a-tuply positively charged cation, and
a is an integer not less than 1.

The process makes it possible to carry out the reaction without distillative recovery of the silane of general formula I (reaction product) having to be preceded by filtration or distillative removal of a solvent, or both.

DETAILED DESCRIPTION OF THE PREFERRED EMBODIMENTS

The high-boiling solvent HBS is present during the distillative removal of the silane of general formula I, and can be added before and/or during the distillative step.

The leaving group X, which is substitutable by the carboxylate group of the compound of general formula II, is preferably a halogen atom, an alkylsulfate group, an alkylsulfonate group, an arylsulfonate group or a reaction product of an alcohol onto an azodicarboxylate, more preferably a chlorine, bromine or iodine atom, a methanesulfonate, p-toluenesulfonate, p-chlorosulfonate or benzenesulfonate group and even more preferably is a chlorine atom. X is preferably attached to a carbon atom, preferably to a $CH_2$ unit, within $R^2$.

$R^1$, $R^2$ and $R^3$ may independently contain one or more heteroatoms, may be interrupted by heteroatoms, may be substituted by heteroatom-containing groups Q, may be cyclic or acyclic or oligocyclic or have cyclic or acyclic or oligocyclic groups, may be saturated or have olefinic or alkynic or aromatic unsaturation, and may be linear or branched or attached to one another.

$R^1$ preferably attaches to the group C(=O) through a carbon atom, or is preferably a hydrogen atom. $R^1$ has preferably from 1 to 12, more preferably from 1 to 8 and most preferably from 1 to 6 carbon atoms, or is a hydrogen atom. $R^1$ has preferably from 0 to 3 and more preferably 0 or 1 and most preferably no heteroatoms. $R^1$ has preferably from 0 to 3, more preferably 0 or 1 and most preferably no substituents Q. Preferably, represents the groups H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)(CH_2CH_3)$, $C(CH_3)_3$ $CH_2CH_2CH_2CH_2$ $CH_3$ $CH_2CH_2CH_2CH_2CH_2CH_3$, $CH_2CH_2CH_2CH_2CH_2CH_3$, $CH_2CH_2CH_2CH_2CH_2CH_2CH_3$, $CH_2CH_2C$ $CH_2CH_2CH_2CH_2CH_2CH_3$, $CH_2CH_2CH_2CH_2CH_2CH_2CH_2$ $CH_2CH_2CH_3$, $CH_2CH_2CH_2CH_2CH_2CH_2CH_2CH_2CH_2$ $CH_3$, $CH_2CH_2CH_2CH_2CH_2CH_2CH_2CH_2CH_2CH_2CH_3$, $CH=CH_2$, $C(CH_3)=CH_2$, cis-CH=CHCH_3, trans-CH=CHCH_3, $CH_2CH_2CH_2CH_2C$ $CH_2CH_2CH_2CH_2CH_2$ =CH_2, phenyl, benzyl, o-methylphenyl, m-methylphenyl, p-methylphenyl, preferably the groups H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)(CH_2CH_3)$, $C(CH_3)_3$, $CH_2CH_2CH_2$ $CH_3$, $CH_2CH_2CH_2CH_2CH_3$, $CH_2CH_2CH_2CH_2CH_2$ $CH_3$, CH=CH_2, $C(CH_3)=CH_2$, cis-CH=CHCH_3, trans-C=CHCH_3, $CH_2CH_2CH_2CH_2CH_2CH_2CH_2CH=CH_2$, phenyl, benzyl, more preferably the groups H, $CH_3$, CH=CH_2, $C(CH_3)=CH_2$, cis-CH=CHCH_3, trans-CH=CHCH_3.

$R^2$ preferably attaches to the silicon atom through a carbon atom, preferably through a $CH_2$ unit, to the group X. $R^2$ has preferably from 1 to 12, more preferably from 1 to 8 and most preferably from 1 to 4 carbon atoms. $R^2$ has preferably from 0 to 3, more preferably 0 or 1 and most preferably no heteroatoms. $R^2$ has preferably from 0 to 3, more preferably 0 or 1 and most preferably no substituents Q. Preferably, $R^2$ represents the groups
—$CH_2CH_2CH_2CH_2$—, —$CH_2$—, —$CH_2CH_2$—, —$CH_2CH_2CH_2$—, phenylene- or —$CH_2$-p-phenylene-, preferably the groups —$CH_2$— or —$CH_2CH_2CH_2$—, and more preferably —$CH_2$—.

$R^3$ is preferably a $C_1$-$C_{12}$ hydrocarbon group, a $C_1$-$C_{12}$ hydrocarbonoxy group or an $Si_1$-$Si_4$ siloxy group, more preferably a $C_1$-$C_6$ alkyl group, a phenyl group or a $C_1$-$C_6$ alkoxy group and most preferably methyl, methoxy or ethoxy. Preferably, at least one of the $R^3$ radicals is a hydrocarbonoxy group. $R^3$ preferably has from 0 to 3, more preferably 0 or 1 and most preferably no substituents Q. When $R^3$ is an $Si_1$-$Si_4$ silane group or an $Si_1$-$Si_4$ siloxy group, the silicon atoms in these groups are preferably substituted by $C_1$-$C_{12}$ hydrocarbon groups, which may optionally have Q or X groups, by hydrogen, or by $C_1$-$C_{12}$ hydrocarbonoxy groups, more preferably by optionally X-containing $C_1$-$C_6$ alkyl groups, by phenyl groups or $C_1$-$C_6$ alkoxy groups, and most preferably by optionally X-containing methyl groups or by propyl groups which optionally have X groups in the terminal position, or by methoxy or ethoxy groups.

$M^{a+}$ is preferably an alkali metal ion, an alkaline earth metal ion, or an onium ion such as for example an optionally alkylated, arylated or substituted ammonium ion, phosphonium ion, amidinium ion or guanidinium ion, preferably lithium, sodium, potassium, magnesium, calcium, an optionally alkylated, arylated or substituted ammonium ion, phosphonium ion, amidinium ion or guanidinium ion, and more preferably sodium, potassium, an optionally alkylated, arylated or substituted ammonium ion, phosphonium ion, amidinium ion or guanidinium ion.

When $M^{a+}$ is an optionally alkylated, arylated or substituted ammonium ion, the ammonium carboxylate is preferably produced before or during the reaction with the silane of general formula III by reacting a carboxylic acid $R^1$—C(=O)—OH with ammonia or with an amine.

a is preferably from 1 to 4, more preferably from 1 to 2 and especially 1.

Q when attached to an $sp^3$-hybridized carbon atom is selected from hydrocarbonoxy, acyloxy, hydrocarboncarbonyl, carbonyl, hydrocarbonoxycarbonyl, hydrocarbonsulfide, acylsulfide, cyano and nitro groups,
and when attached to an $sp^2$- or to an sp-hybridized carbon atom, is selected from hydrocarbonoxy, acyloxy, hydrocarboncarbonyl, carbonyl, hydrocarbonoxycarbonyl, hydrocarbonsulfide, acylsulfide, cyano and nitro groups and from the meanings of X as defined above. By "interrupted by heteroatoms" is meant that heteroatoms may be bonded between carbon atoms of the respective hydrocarbon groups or in the case of Si compounds, between otherwise adjacent Si atoms.

The carboxylic acid salt of general formula II preferably has a water content of less than 10,000 ppm, more preferably less than 1000 ppm and most preferably less than 100 ppm. The carboxylic acid salt of general formula II preferably has a free carboxylic acid content of less than 10%, more preferably less than 1% and most preferably less than 0.1%. The carboxylic acid salt of general formula II preferably has a content of basic impurities, for example alkali or alkaline earth metal hydroxides, oxides, carbonates or bicarbonates, of less than 10%, more preferably less than 1% and most preferably less than 0.1%. Before or during use in the process of the present invention, the carboxylic acid salt can be dried, for example by azeotroping with a water-entraining solvent, by heating, by applying a vacuum, by storage over a drier, by a dry stream of gas or liquid, or by a combination thereof.

The process preferably utilizes exactly one silane of general formula III. The term "exactly one silane of formula III" here is defined by the purity of the silane of general formula III. The purity of the silane of general formula III is preferably more than 80%, more preferably more than 90% and even more preferably more than 97%, in weight % based on the sum total of all silanes of general formula III which are present in the process. However, it is also possible to use a mixture of two or more silanes of general formula III. The process preferably utilizes exactly one carboxylic acid salt of general formula II. The term "exactly one carboxylic acid salt of general formula II" is here defined via the purity of the carboxylic acid salt of general formula II. The purity of the carboxylic acid salt of general formula II is preferably more than 80%, more preferably more than 90% and most preferably more than 97%, in weight % based on the sum total of all carboxylic acid salts of general formula II which are present in the process plus their carboxylic acid derivatives. But it is also possible to use a mixture of two or more carboxylic acid salts of general formula II.

When the silanes of general formula III or the carboxylic acid salts of general formula II have isomers, for example constitutional or configurational isomers, it is their effect on the planned use of the reaction product which determines whether none, one or more of the isomers are or are not considered as impurity in the purity calculation.

The process is preferably carried out in the presence of catalysts. Phase transfer catalysts for example can be useful, especially when the solvent or solvent mixture used is so apolar that, in a mixing test, it has a miscibility gap with water at 20° C., i.e., there is a ratio of water to solvent at which the two are not fully homogeneously miscible.

Examples of phase transfer catalysts useful for reactions of carboxylate ions of carboxylic acid salts of general formula II are salts which, in addition to their anions, have cations that bear hydrocarbon groups, preferably $C_1$-$C_{40}$ hydrocarbon groups. When the cation of the catalyst has two or more hydrocarbon groups, it is preferable for at least one of these groups to be a $C_2$-$C_{40}$ hydrocarbon group, more preferably for at least one of these groups to be a $C_4$-$C_{40}$ hydrocarbon group and most preferably for two, three, four or more of these groups to be $C_4$-$C_{40}$ hydrocarbon groups.

The cation of the catalyst is preferably a tetra($C_1$-$C_{40}$-alkyl) ammonium, benzyltri($C_1$-$C_{40}$-alkyl) ammonium, ($C_1$-$C_{40}$-alkyl)pyridinium, tetra($C_1$-$C_{40}$-alkyl)guanidinium, hexa($C_1$-$C_{40}$-alkyl) guanidinium, tetra($C_1$-$C_{40}$-alkyl)-phosphonium, benzyltri($C_1$-$C_{40}$-alkyl)phosphonium or triphenyl($C_1$-$C_{40}$-alkyl)phosphonium ion and also a benzyltriphenylphosphonium ion, in which case the $C_1$-$C_{40}$ alkyl chains as a whole can independently be structurally the same or different and the individual $C_1$-$C_{40}$ alkyl chains of a cation may be structurally unitary or mixtures of two or more structurally different alkyl chains. Examples are the tetraethylammonium, tetrabutylammonium, tetrahexyl-ammonium, tetraoctylammonium, trimethyltetradecyl-ammonium, tributylmethylammonium, tributylhexa-decylammonium, trioctylmethylammonium, trioctylpropyl-ammonium, dimethyldioctadecylammonium, benzyltrimethyl-ammonium, benzyltriethylammonium, benzyltributyl-ammonium, benzyldimethyldodecylammonium, tetramethyl-guanidinium, hexaethylguanidinium, tetrabutylphosphonium, tetraoctylphosphonium, tri(isobutyl)methyl-phosphonium, tributyltetradecylphosphonium, tributyl-hexadecylphosphonium, trihexyltetradecylphosphonium, trioctylethylphosphonium, benzyltributylphosphonium and triphenylmethylphosphonium ion.

The anion of the catalyst is preferably a halide, sulfate, hydrogensulfate, alkylsulfate, alkanesulfonate, aromatic sulfonate, carboxylate, bicarbonate, carbonate, hydroxide, aryl oxide or alkoxide ion,
more preferably a fluoride, chloride, bromide, iodide, sulfate, hydrogensulfate, methylsulfate, laurylsulfate, methanesulfonate, benzenesulfonate, p-toluenesulfonate, formate, acetate, benzoate, bicarbonate, carbonate or hydroxide ion, most preferably a chloride, bromide, iodide, hydrogensulfate or acetate ion.

The phase transfer catalyst can also be produced in situ by reacting an acid, for example a carboxylic acid $R^1$—C(=O)—OH, with a base to form the corresponding acid-base salt wherein the resulting Brønsted acid corresponding to the base satisfies the conditions mentioned above for the cation of the phase transfer catalyst; examples of suitable bases are 1,8-diazabicyclo[5.4.0]undec-7-ene (DBU), 1,5-diazabicyclo-[4.3.0]non-5-ene (DBN), 1,4-diazabicyclo[2.2.2]octane (DABCO), trioctylamine, tributylamine, triethylamine, ethyldiisopropylamine, dicyclohexylamine, hexylamine, tetramethylguanidine. The phase transfer catalyst can further be produced in situ by using an amine, a phosphine or a sulfide capable of reacting with the X—$R^2$— group in the silane of general formula III to form, by substitution of X, the corresponding ammonium, phosphonium or sulfonium salt which can then act as phase transfer catalyst. The latter method of producing the phase transfer catalyst in situ can optionally also employ a different alkylating agent as silane of general formula III.

The aforementioned phase transfer catalysts engender an exchange of [$M^{a+}$] with one or more cations of the phase transfer catalyst, so that the resulting new carboxylic acid salt, the cation of which is the cation of the phase transfer catalyst, constitutes the reactive species; this new salt is generally more soluble in the reaction mixture than the carboxylic acid salt originally used.

Useful phase transfer catalysts further include crown ethers, cryptands or coronands, for example 18-crown-6 or 15-crown-4. These are preferably used in combination with carboxylic acid salts of general formula II which have an alkali or alkaline earth metal cation, especially an alkali metal cation. These phase transfer catalysts can combine with the metals to form complexes, for example 1:1 or 1:2 complexes, which together with the carboxylate ion have an improved solubility, speeding the reaction.

Preferred phase transfer catalysts are tetrabutylphosphonium chloride, tetrabutylphosphonium bromide, tetrabutylammonium bromide, tributylmethylammonium chloride, methyltri($C_8$-$C_{10}$-alkyl) ammonium chloride, dimethyldi ($C_{16}$-$C_{18}$-alkyl) ammonium chloride, benzyl-trimethylammonium chloride, benzyltriethylammonium chloride, trihexyltetradecylphosphonium chloride, hexaethylguanidinium chloride and hexaethylguanidinium bromide. Phase transfer catalysts are available for example under the trade names Cyphos® (from Cytec), Aliquat® (from Cognis), Arquad® (from Akzo Nobel) or PräPagen® (from Clariant), for example the types Cyphos® IL164, Cyphos® IL163, Cyphos® IL101, Aliquat® 100, Aliquat® 134, Aliquat® 336, Aliquat® 175, Aliquat® HTA-1, Arquad® 2HT-75 or PräPagen® WK.

The catalysts may be for example activators for the group X in the silane of general formula III. Preference for this is given to using salts of iodide or of bromide, or more preferably salts of iodide, for example lithium bromide, lithium iodide, sodium bromide, sodium iodide, potassium bromide or potassium iodide. These salts are capable of replacing the group X by a bromine atom or by an iodine atom, so that the resulting bromoalkyl group Br—$R^2$—, or the resulting iodoalkyl group I—$R^2$—, on the silicon atom has particularly high reactivity with regard to carboxylate ion, present in the carboxylic acid salt of general formula II.

The amount of catalyst used, based on the amount of substance used of silane of general formula III, is preferably in the range from 0.01 to 30 mol %, more preferably in the range from 0.1 to 10 mol % and especially in the range from 0.5 to 5 mol %. When two or more silanes of general formula III are used, these ranges are based on the sum total of the amounts of substances of all silanes used of general formula III. The water content of the catalysts is preferably less than 10%, more preferably less than 1% and most preferably less than 0.1%. Catalysts can be dried during or before use in the process of the present invention, for example by azeotroping with a water-entraining solvent, by heating, by applying a vacuum, by storing over a drier, by a dry stream of gas or liquid or by any combination thereof.

Catalysts can be used individually or as mixtures of two, three or more catalysts. Catalysts can be used as a discrete substance or as a solution, for example in water, alcohols such as methanol, ethanol, 2-propanol, hydrocarbons, ethers, or esters. Any solvents used to dissolve the catalysts can be removed by distillation, for example, before, during or after the process according to the present invention. Solvents are preferably removed before the process of the present invention if they disrupt the reaction, for example when the solvent of the phase transfer catalyst contains water and the silane of general formula III contains hydrolyzable groups $R^3$, or when the solvent of the phase transfer catalyst has a similar boiling point to the silane of general formula I, i.e., more particularly when the boiling point of the solvent is less than 40 K above or below the boiling point of the silane of general formula I, as measured at the pressure at which the distillative step is carried out.

Solvents used preferably have a boiling point that is sufficiently different from the boiling point of the silane of general formula I to allow simple distillative separation.

The solvents or solvent mixtures for use in the process are characterized in that they contain/include at least one high-boiling solvent "HBS" which, as measured at the pressure for performing the abovementioned distillative step where the distillate contains at least one silane of general formula I, has a higher boiling point than the silane of general formula I (hereinafter referred to as "boiling point condition"). Preferably, at least one solvent constituent that complies with this criterion has a boiling point which, as measured at the pressure at which the abovementioned distillative step is carried out, is at least 10 K higher than the boiling point of the silane of general formula I, preferably at least 20 K higher and more preferably at least 30 K higher. If the mixture contains two or more solvents that satisfy the conditions for HBS, then the proportion of all HBS's in total that boil at less than 10 K higher than the silane of formula I is preferably less than 10%, more preferably less than 5% and most preferably less than 1%; the proportion of all HBS's in total that boil at less than 20 K higher than the silane of general formula I is preferably less than 20%, more preferably less than 10% and even more preferably less than 2%; the proportion of all HBS's in total that boil at less than 30 K higher than the silane of general formula I is preferably less than 40%, more preferably less than 20% and even more preferably less than 5%, all in weight % based on the sum total of all HBS's used, subject to the proviso that the boiling points are measured at the pressure at which the abovementioned distillative step is carried out. The proportion of solvents that comply with the criteria for HBS, based in weight % on the sum total of all solvents used in the process, is preferably at least 20%, more preferably at least 50% and most preferably at least 80% in the process. Preferably, the process does not utilize any solvents that boil at less than 10 K higher than the silane of general formula I, preferably no solvents that boil at less than 20 K higher than the silane of general formula I and more preferably no solvents that boil at less than 30 K higher than the silane of general formula I, subject to the proviso that the boiling points are measured at the pressure at which the abovementioned distillative step is carried out. When a solvent mixture contains an undesirably high proportion of constituents whose boiling point is undesirably close to the boiling point of the silane of general formula I, the solvent mixture can be subjected before use to incipient stripping, i.e., a low-boiling cut is separated off and the higher-boiling cut or the remaining bottom product, consisting of or containing HBS, is used as solvent in the process of the present invention.

The solvents used, especially those satisfying the boiling point condition for HBS, are preferably inert to the reactants, catalysts, products and any further admixtures involved in the reaction and the distillative step under the conditions of the reaction and of the distillative step, or are converted into inert compounds by the reactants or optionally by other components; preferably, they are inert.

Examples of inert classes of compound which are usable as solvents (for example as HBS, if they satisfy the boiling point condition) with preference are saturated or olefinically or aromatically unsaturated, linear or branched, cyclic or acyclic or oligocyclic or cyclic group-containing hydrocarbons, ethers, carboxylic esters, amides such as carboxamides or phosphoramides, carbamates, sulfoxides, sulfones, ureas, lactones, lactams, N-alkyllactams, ionic solvents, alkyl- or aryl-terminated silicone oils such as, for example, trimethylsilyl-terminated silicone oils; preference among the solvents mentioned is given to linear or branched, cyclic or acyclic, saturated or aromatically unsaturated hydrocarbons, ethers, carboxylic esters, amides, sulfoxides, sulfones, ureas, ionic solvents or alkyl- or aryl-terminated silicone oils. Particular preference is given to linear or branched, cyclic or acyclic, saturated or aromatically unsaturated hydrocarbons or alkyl-silyl-terminated silicone oils.

Examples of preferred solvents which can be used (for example as HBS, if they satisfy the boiling point condition) are the isomers, especially the n-isomers of decane, undecane, dodecane, tridecane, tetradecane, pentadecane, hexadecane, heptadecane, octadecane, nonadecane, eicosane, heneicosane, docosane, tricosane, tetracosane, pentacosane, hexacosane, heptacosane, octacosane, nonacosane, triacontane, $C_{31}$-$C_{100}$ hydrocarbons, hydrocarbon mixtures such as paraffins, solvents of the White Spirit, Low Aromatic White Spirit, High Aromatic White Spirit, High Flash White Spirit, crystal oil, SBP, Shellsol® or Sarasol® range from Shell (for example Shellsol® D40, D43, D60, DSC, D70, D80, D90, D100, D100S, D120, A100, A150, A150ND, TC, TD, OMS, T, TK, TM, B HT, 7 EC, 15, 16, H, 2325, 2046, 1495; Sarasol® 40, 75, 85, 120; SBP 140/165), solvents of the Hydroseal, Isane, Ketrul®, Kerdane®, Spridane® or Solvarex® range from Total (for example Hydroseal G400H, G340H, G3H, G250H, G240H, G232H; Ketrul D100, 220, 212, 211, D85, D80, D75, D70, HT; Spirdane D66, K2, D60L, D60, D40K, D40, HT, D30, L1, D25; Isane IP185, IP175, IP165, IP155, IP130; Solvarex 9, 10, 10LN), heat transfer oils (for example Marlotherm® SH, from AVIA), plasticizer oils (for example Exarol®, Plaxene® or Plaxolene® range from Total), waxes, N,N-dimethylformamide, N-methylformamide, formamide, dimethyl sulfoxide, N-methylpyrrolidone, dimethylpropyleneurea (1,3-dimethyl-3,4,5,6-tetrahydro-2 (1H)-pyrimidinone), tetramethylurea, urea, α,ω-bis(trimethylsilyl)-terminated poly(dimethylsiloxane)s such as for example the silicone oils AK 35, AK 50, AK 100, AK 200, AK 350, AK 1000, AK 10000, AK 12500, AKF 1000, AKF 10000 (all Wacker Chemie AG), poly(dimethylsiloxane-co-methylphenylsiloxane) such as for example AP 100, AP 200, AP 1000, AS 100, AR 200 (all Wacker Chemie AG), functional silicone oils such as Wacker L 051 silicone oil, ADVALON® PN 100, FA 33, PS 500 (all Wacker Chemie AG), ethylene glycol dibutyl ether, diethylene glycol dimethyl ether, diethylene glycol dibutyl ether, triethylene glycol dimethyl ether, triethylene glycol dibutyl ether, tetraethylene glycol dimethyl ether, dialkyl ethers such as dibutyl ether, dioctyl ether, diphenyl ether, dibenzyl ether; polyethylene glycols, polypropylene glycols or polyethylene glycol-polypropylene glycol copolymers which are ether or ester terminated, or mixedly ether and ester terminated, at both ends of the chain; esters of $C_4$-$C_{30}$ fatty acids or diesters of $C_4$-$C_{30}$ dicarboxylic acids, especially of $C_8$-$C_{22}$ fatty acids or $C_8$-$C_{22}$ dicarboxylic acids, for example the methyl, ethyl, n-propyl, isopropyl, n-butyl, sec-butyl, isobutyl, tert-butyl, n-pentyl, n-hexyl, n-heptyl, n-octyl, phenyl, benzyl or $C_8$-$C_{22}$-alkyl esters of butanoic, hexanoic, octanoic, decanoic, dodecanoic, tetradecanoic, hexadecanoic, octadecanoic, eicosanoic, docosanoic, succinic, adipic or suberic acid, triesters of glycerol such as glycerol triacetate or glycerol tributyrate for example, or diesters of phthalic acid such as dibutyl phthalate, dioctyl phthalate, dinonyl phthalate or diisononyl phthalate for example; among the solvents mentioned, it is the hydrocarbons and the silicone oils which count as particularly preferred solvents. Further solvents appear in Directory of Solvents, (B. P. Whim, P. G. Johnson, editors), First Edition 1996, Blackie Academic & Professional (Chapman & Hall, London, Weinheim, N.Y., Tokyo, Melbourne, Madras), ISBN 0-7514-0245-1.

The solvents used, including those satisfying the boiling point condition for HBS, do not necessarily have to be inert to the reactants, catalysts, products and any further admixtures involved in the reaction and the distillative step under the conditions of the reaction and the distillative step.

Examples of noninert solvents that can nonetheless be used in the process are for instance compounds having alcohol, silanol or carboxylic acid functions. Alcohols can for example, when at least one of the $R^3$ groups in the silane of general formula I or of general formula III represents a hydrolyzable group, react with the silane by exchanging $R^3$ for the alkoxy radical corresponding to the alcohol, in which case $R^3$—H is released. Carboxylic acids can for example, when at least one of the $R^3$ radicals represents an alkoxy radical, react with this alkoxy radical to form the corresponding carboxylic ester and siloxane, or they can enter a proton transfer with the carboxylic acid of general formula II. Silicone oils with silanol groups can, when at least one of the $R^3$ radicals represents a hydrolyzable radical, react with the silanes of general formula I or of general formula III to form the corresponding silane-terminated silicone oils, in which case $R^3$—H is released. Protic compounds can solvate the carboxylic acid salt and influence the rate of reaction; if a preliminary test shows that a protic solvent has an adverse effect on the rate of reaction, i.e., slows the reaction, it is preferably replaced by another solvent. When noninert solvents are used, the number of reactive groups in the noninert solvent and in the silanes of general formulae I and III is preferably determined such that preferably no crosslinking occurs due to the above-described reactions for example. The reactions of noninert solvents can change the boiling points of these solvents, so that solvents that satisfy the boiling point condition for HBS may possibly be formed in situ. Noninert solvents may possibly become converted into inert solvents as a result of reaction with other components in the process. For example, solvents with alcohol or silanol functions can be silylated by silanes of general formulae I and III if these contain hydrolyzable groups $R^3$ (the silylation generally involving detachment of $R^3$—H), so that the silylated alcohol or silanol function in the solvent is inert under the reaction conditions. When the concentration of functional groups in the solvent is low, for example in polyethylene glycols, polypropylene glycols, poly(ethylene glycol-co-propylene glycols, monoalkylated or monoesterified glycols or oligoethylene glycols (for example Brij 35, 52, 56, 72, 76, 92 V, 93, 96 V, 97, 98, 78 P, 58, 700) or in silanol-functional silicone oils, the extent of silanes of general formulae I and III which are lost as a result of hydrolyzable groups $R^3$ reacting with such solvents can be low and hence tolerable. In general, solvents are recycled, so that, if originally noninert solvents have been converted into inert solvents in the process, the recycled solvents thus produced can be used as inert solvents.

It is further possible to use for example triesters of phosphoric acid, such as tributyl phosphate or trioctyl phosphate, or diesters of phosphoric acids, as solvents, for example as HBS, in which case these solvents can exchange ester/alkoxy groups with the silanes of general formula I or alkoxy groups with the silanes of general formula III, depending on the conditions employed for the reaction procedure and the distillative step.

Solvents used can also act as compatibilizers, for example by enhancing the solubility of catalysts, carboxylic acid salts of general formula II, silane of general formulae I or III in each or one another or in other solvents used. Suitable for this purpose can be for example linear polyethers, for example polyethylene glycols or polypropylene glycols or copolymers thereof, or singly or doubly ester- or ether-terminated polyethylene glycols or polypropylene glycols such as, for example, polyethylene glycol dimethyl ether, ethylene glycol dimethyl ether or dibutyl ether, diethylene glycol dimethyl ether or dibutyl ether, triethylene glycol dimethyl ether or tetraethylene glycol dimethyl ether. To achieve solubility enhancement for the carboxylic acid salt of general formula II, it is preferable for temperatures above 80° C., more preferably above 120° C. and most preferably above 160° C. to be employed here.

The solvents used can be halogenated solvents, for example chlorinated solvents. It is preferable for the halogenated solvents to be unreactive with the starting materials under the conditions of the process and it is more preferable for the halogen function of halogenated solvents to be unreactive with the carboxylate in the carboxylic acid salt of general formula II under the conditions of the process. Expressed as a proportion of the sum total of all solvents used, preferably less than 50%, more preferably less than 20% and especially less than 5% of the solvents used are halogenated. In a particularly preferred embodiment, no halogenated solvents are used in the process.

Solvents need not be liquid at room temperature to be successfully used in the process of the present invention. Paraffins for instance, which can have melting points of around 70° C., are perfectly useful, for example as HBS, provided they satisfy the boiling point condition. Even higher-melting solvents are useful as solvents and also, provided they satisfy the boiling point condition, as HBS; they merely need to liquefy under the conditions of the distillative step if they are to be used as HBS. For practical reasons (melting open and heating of lines is unnecessary or facilitated), the solvents or solvent mixtures preferably have melting points/ranges below 30° C., more preferably below 20° C. and even more preferably below 10° C. High-melting solvents or solvent mixtures can be converted into lower-melting solvent mixtures, for example into eutectic mixtures, by blending with other solvents or solvent mixtures for example.

Solvents can be used alone, or two, three or more solvents, of which one, two, three or more satisfy the boiling point condition applicable to HBS, can be used in the process. It is optionally also possible for the process to additionally utilize solvents which do not satisfy the boiling point condition, i.e., which under the conditions of the distillative step have a boiling point equal to or below that of the silane of general formula I. Such solvents distill over in the distillative step before or with the fraction that contains silane of general formula I, depending on the separation efficiency, the relative position of boiling points and the appearance of any azeotropes. Preferably, less than 80%, more preferably less than 50% and especially less than 20%, of solvents used in the process have a boiling point in the distillative step which is equal to or below that of the silane of general formula I, calculated in weight % based on the sum total of all solvents used in the process, wherein the boiling points are measured at the pressure at which the distillative step is carried out, where the distillate contains at least one silane of general formula I.

Preferably, the process utilizes no solvent with a boiling point equal to or below that of the silane of general formula I, especially no solvent having a boiling point equal to that of the silane of formula I, wherein the boiling points are measured at the pressure at which the abovementioned distillative step is carried out.

At least one solvent satisfying the above-defined boiling point condition for HBS is added in the process in at least one step, optionally even in two or more steps, but at the latest in the course of the distillative step, which is described hereinbelow; addition is also possible at an earlier stage of the process.

The process preferably employs less than 10% of solvents that combine with the silane of general formula I to form a binary azeotrope or combine with the silane of general formula I and further substances in the mixture to form a ternary, quaternary or higher azeotrope, preferably less than 1% and more preferably less than 0.1%, in weight % based on the theoretical yield of silane of general formula I. A particularly preferred embodiment employs no solvents that form such azeotropes. Preferably, the proportion of such solvents in total that boil at less than 10 K lower than the silane of general formula I is preferably less than 10% or more preferably less than 5% and most preferably less than 1%; the proportion of such solvents in total that boil at less than 20 K lower than the silane of general formula I is preferably less than 20% or more preferably less than 10% and most preferably less than 2%; the proportion of such solvents in total that boil at less than 30 K lower than the silane of general formula I is preferably less than 40% or more preferably less than 20% and most preferably less than 5%, based on the sum total of all solvents used, where the boiling points are measured at the pressure at which the abovementioned distillative step is carried out. The process preferably employs no solvents boiling at less than 10 K lower than the silane of general formula I, preferably no solvents boiling at less than K lower than the silane of general formula I and preferably no solvents boiling at less than 30 K lower than the silane of general formula I, subject to the proviso that the boiling points are measured at the pressure at which the abovementioned distillative step is carried out.

Solvent mixtures can behave differently than pure solvents. Similarly, the presence of reaction components of the process, for example silanes of general formulae I or III, can influence the boiling behavior of the solvents used, and vice versa. The formation of any azeotropes is difficult to foresee for instance. Yet which solvents alone or in admixture are useful as high boiler solvent HBS is readily ascertainable by a person skilled in the art in a suitable preliminary test, for example by admixing the mixture of the reaction to be carried out in the process (formulae II+III-->I) with the desired solvents and testing the boiling behavior in admixture.

It is sensible for this first to determine the boiling point of the silane of general formula I at the pressure at which the distillative step is to be carried out later. To test the boiling behavior, the test mixture is admixed with at least one solvent which, based on its boiling point as pure substance at this pressure, has a higher boiling point than the silane of general formula I (i.e., a solvent that satisfies the boiling point condition for HBS). Unless otherwise stated, the pressure employed is 100 mbar, 20 mbar or 1 mbar. When particularly preferred solvents are employed as HBS which at the pressure of the distillative step have a distinctly higher boiling point than the silane of general formula I (boiling point difference at least 30 K), there is generally no need to carry out preliminary tests.

The water content of solvents used in the process is preferably less than 10,000 ppm, more preferably less than 1000 ppm and most preferably less than 100 ppm. Solvents used can be dried during or preferably before use in the process of the present invention, for example by azeotroping with another water-entraining solvent, by azeotroping when the solvent itself acts as water entrainer, by incipient stripping or by incipient distilling, by heating, by applying a vacuum, by storing over or distilling from a drier or by a combination thereof.

The total amount in which the HBS high boiling solvents which satisfy the boiling point condition are used is preferably equal to between one-twentieth and twenty times the total mass of employed silanes of general formula III, more preferably between one-tenth and five times, and most preferably between one-fifth and two times.

The process preferably employs solvents which are not classed as hazardous to health, toxic, extremely toxic, carcinogenic, mutagenic, teratogenic, as an odor nuisance, irritant or caustic.

The solvents used in the process, especially the HBS high boiling solvents which satisfy the boiling point condition, can be immiscible or partially or completely miscible with each or one another and with one or more of the starting materials and products and catalysts or be insoluble or partially or completely soluble in each or one another. For a successful process it is generally sufficient for at least a proportion of the carboxylate from the carboxylic acid salt of general formula II to come into contact with at least a proportion of the silane of general formula III at a phase boundary or preferably within a homogeneous phase. Dynamic phase equilibria ensure that the starting materials will over time come to react in full even if only proportions come into contact with each or one another at any one time.

The process is preferably carried out under an inert atmosphere, preferably under an argon or nitrogen atmosphere. The water content of the atmosphere is preferably less than 10,000 ppm, more preferably less than 1000 ppm and most preferably less than 100 ppm. The oxygen content of the atmosphere is preferably less than 10,000 ppm, more preferably less than 1000 ppm and most preferably less than 100 ppm.

The reaction of the carboxylic acid salt of general formula II with the silane of general formula III can be carried out with cooling, at ambient temperature or at elevated temperature, preferably at not less than 0° C., more preferably at not less than 30° C., and most preferably at not less than 50° C. and preferably at not more than 300° C., more preferably at not more than 250° C. and most preferably at not more than 200° C.

Cooling can be effected for example by jacket, stirrer or evaporative cooling, heating for example by jacket or stirrer heating, heat transfer can be effected for example electrically, with brine, oil, water, optionally superheated steam or by shearing/friction.

The reaction can generally be carried out at atmospheric pressure ±50 kPa; the reaction pressure is preferably in the range from 0.1 Pa to 100 MPa, more preferably in the range from 100 Pa to 10 MPa and even more preferably in the range from 10 kPa to 1 MPa. The reaction can be carried out for example as a batch reaction, discontinuously, continuously, cascadingly, in residence time reactors, residence time tubes or in mixers (for example dynamic or static mixers).

The reaction can be carried out without solvent or in the presence of one or more solvents. The solvents can comply with the criteria for HBS for example. Solvents used preferably have a water content of less than 10,000 ppm, more preferably less than 1000 ppm and most preferably less than 100 ppm.

The reaction mixture is preferably commixed, for example by convection or stirring. The reaction can be carried out in mono- or polyphasic mixtures, for example in mono-, di- or triphasic mixtures, for example solid/liquid, gaseous/liquid, liquid/liquid, solid/liquid/liquid. For instance, a solvent can form a liquid phase, which optionally contains dissolved fractions of reactants, a catalyst-silane mixture can contain a second liquid phase, which contains dissolved fractions of the carboxylic acid salt of general formula II and optionally solvent, and the carboxylic acid salt can form a third phase which is solid for example.

The order of adding carboxylic acid salt of general formula II, silane of general formula III, optionally catalysts, solvents, optionally stabilizers, although freely choosable in principle, is determined by practical aspects which a person skilled in the art can ascertain in range-finding tests. For example, all the components can be included in the initial charge and heated up, or one or more components are initially charged while the others are metered in, or all components are simultaneously metered in and commixed, for example portionwise or continuously.

In a preferred first embodiment, at least one carboxylic acid salt of general formula II is initially charged and at least one silane of general formula III is metered in with or without heating.

In a preferred second embodiment, at least one silane of general formula III is initially charged and at least one carboxylic acid salt of general formula II is metered in with or without heating.

In a preferred third embodiment, the procedure of the first or second embodiment is adopted and additionally at least one catalyst is included in the initial charge.

In a preferred fourth embodiment, the procedure of the first or second embodiment is adopted and additionally at least one catalyst is metered in.

In a preferred fifth embodiment, the procedure of the first, second, third or fourth embodiment is adopted and additionally at least one solvent which preferably complies with the criteria for HBS is included in the initial charge.

In a preferred sixth embodiment, the procedure of the first, second, third or fourth embodiment is adopted and additionally at least one solvent which preferably complies with the criteria for HBS is metered in.

The reaction is preferably carried out by using the silane of general formula III in an approximately or exactly stoichiometric proportion relative to the amount of carboxylic anions in the carboxylic acid salt of general formula II. When the silane of general formula III has two or more substitutable leaving groups X, or when two or more different silanes of general formula III are used, this stoichiometry is generally calculated on the basis of total leaving groups X. When two or more different carboxylic acid salts of general formula II are used, this stoichiometry is generally calculated on the basis of total carboxylate ions. Approximately stoichiometric is to be understood as meaning that the ratio of groups X in the silanes of general formula II to carboxylate ions in the carboxylic acid salts of general formula III is preferably in a ratio of 2.0:1.0 to 1.0:2.0, more preferably 1.5:1.0 to 1.0:1.5 and most preferably 1.2:1.0 to 1.0:1.2. In a particularly preferred embodiment, this ratio is 1.0:1.0. The reaction is preferably run such that at least 80%, preferably at least 90% and especially at least 95% of the employed carboxylic acid salts of general formula II or of the employed silanes of general formula II are converted, these percentages being based on the starting material which is used in deficiency when the carboxylic acid salts of general formula II have not been used in exactly the stoichiometric ratio relative to the silanes of general formula II (i.e., not in the abovementioned ratio of 1.0:1.0). Conversion can be enhanced/speeded via longer reaction time, the addition of catalysts or via higher temperatures.

When the silane of general formula III has two or more substitutable leaving groups X, or when two or more different silanes of general formula III with leaving groups X having different reactivities are used, the carboxylic acid salts of general formula II can also be used for example in an amount which only corresponds to the sum total of the most reactive (not all) groups X, permitting specific partial substitution of the leaving groups X in the silane. In another embodiment, substitution of all leaving groups X can be achieved by using an at least corresponding amount of substance of carboxylic acid salt of general formula II.

When the carboxylic acid salt of general formula II has two or more different carboxylate ions, or when two or more different carboxylic acid salts of general formula II are used and carboxylate ions therein have different reactivities, the silanes of general formula III can also be used for example in an amount such that the leaving groups X therein correspond to the sum total of the most reactive (not all) carboxylate ions, permitting specific partial conversion of the most reactive carboxylate ions. In another embodiment, reaction of all carboxylate ions can be achieved by using an at least corresponding amount of substance of silane of general formula III.

While the reaction is ongoing, a distillation can take place at the same time. It can be used for example to remove a lower-boiling solvent, a volatile product or excess starting material.

One or more stabilizers can be added before, during or after the reaction. These can be for example acid or base scavengers (i.e., for example, bases, acids, buffers, amphoterics) or free-radical inhibitors. Free-radical inhibitors which can be added include for example phenol derivatives such as 2,6-di-tert-butyl-4-methylphenol (BHT) or 2,6-di-tert-butylphenol, thiols such as dodecyl mercaptan, or sulfides such as phenothiazine. Oxygen, for example by setting a low oxygen partial pressure, for example $p(O_2)=1$ Pa to 1000 Pa, can be used as an inhibitor, optionally in combination with further free-radical scavengers.

The process includes at least one distillative step. In this step, at least one silane of general formula I is partially or completely separated by distillation from at least one high boiling solvent HBS which, under the conditions of the distillative step, has a higher boiling point than the silane of general formula I. "Partially" here is to be understood as meaning that the mass ratio of silane of general formula I to HBS is greater in the distillate than in the crude mixture prior to distillation. The silane of general formula I passes over more readily into the distillate than HBS; the silane of general formula I accumulates in the distillate and HBS accumulates in the bottom product. Preferably, more than 80% of the silane of general formula I present in the undistilled crude mixture is distilled out of the mixture, preferably more than 90% and more preferably more than 95%. More complete separation of the silane of general formula I from high boiler solvent HBS can be achieved for example by using a higher temperature during the distillation, reduced pressure, an efficient column or an HBS that has a large boiling point difference relative to the silane of general formula I (more preferably more than 30 K above the boiling point of the silane of general formula I under the conditions of the distillative step). In a preferred embodiment, the distillation is carried on until all of the silane of general formula I has been distilled off and all that passes over at the top is a stream mainly containing or consisting of HBS. The process may also include a plurality of, for example two or three, distillative steps.

In general, the earliest point for the distillative step to start is when the reaction has reached the desired conversion of carboxylic acid salt of general formula II and/or silane of general formula III. If the reaction is not carried on to completion, it may also continue during the distillative step, although this is frequently limited because the silane of general formula III is generally removed distillatively from the reaction mixture during the distillation, thereby preventing further reaction with the carboxylic acid salt of general formula II, which generally remains behind in the bottom product. However, when the silane of general formula III has a higher boiling point than the silane of general formula I, the distillative step can advantageously and preferably also be carried out at the same time as the reaction, or temporally overlap the reaction at least partly. For this, the pressure, temperature and separation efficiency are adjusted such in the distillative step that the silane of general formula I distills over and the silane of general formula III stays in the runback or bottom product, where it can react further with the carboxylic acid salt of general formula II. This embodiment is generally a success when the group X is polar and/or has a high molar mass, for example when X is selected from alkyl- or arylsulfonate groups such as methanesulfonate, trifluoromethanesulfonate, benzenesulfonate, p-toluenesulfonate, p-chlorobenzene-sulfonate, and at the same time the group $R^1$ is apolar and/or has a low molar mass, for example when $R^1$ is selected from hydrogen, methyl, ethyl, n-propyl, isopropyl, n-butyl, sec-butyl, tert-butyl, vinyl, 1-methylvinyl or 2-methylvinyl.

The distillative step can be effected for example as batch distillation, continuously, as falling film, short path or thin layer distillation, through columns with separation performance such as, for example, packed or sieve plate columns. The crude mixture to be distilled is for example heated with water, oil, optionally superheated steam or electrically and the distillate is condensed out in a condenser which is air, water or brine cooled for example. Preferably, the distillative step is carried out at a pot or thin layer or film temperature of 30-300° C., preferably 40-260° C. and more preferably 60-220° C. and at a head temperature (as measured at the point when the distillate passes over, shortly before it condenses) of preferably 20-260° C., more preferably 30-220° C. and most preferably 40-180° C. Preferably, the distillative step is carried out at a pressure, as measured in the pot or above the thin layer evaporation or above the evaporation film, of 2 Pa to 500 kPa, preferably 10 Pa to 130 kPa and more preferably 20 Pa to 90 kPa. Preferably, the distillative step is carried out at a pressure, as measured at the point where the distillate passes over, shortly before it condenses, of 1 Pa to 400 kPa, preferably 5 Pa to 120 kPa and more preferably 10 Pa to 80 kPa.

The high boiling solvent HBS can be present in the mixture even before the start of the distillative step, for example when it was added before, during or after the reaction; it can also be added before or during the distillative step. For example, the silane of general formula I can be distilled out of the mixture and the bottom product be kept stirrable and distillable in the meantime by addition of sufficient amounts of HBS.

The reaction mixture can be subjected to the distillative step as obtained for example. Generally, the reaction mixture contains partially or completely undissolved salt $[M^{a+}]X^-_a$. Dissolved salt $[M^{a+}]X^-_a$ can precipitate during the distillative step, for example when the temperature management or the distillatively caused concentrating of the mixture favors precipitation, or undissolved salt $[M^{a+}]X^-_a$ can pass into solution during the distillative step, for example when the temperature management favors solubility or when a polar high boiler solvent HBS is used, for example sulfolane, and an apolar product is distilled out, so that the distillation residue becomes more polar in the course of the distillation. Analogous dissolution/precipitation processes may apply if appropriate to carboxylic acid salt of general formula II which can be present during the distillation, for example when it was used in excess or when it has not been fully converted.

It is preferable for the mixture coming from the reaction of the carboxylic acid salt of general formula II with the silane of general formula III to be fed directly, without further process steps, such as filtration or phase separation for example, into a distillative step. The phases of the mixture to be distilled, however, can optionally be separated before the distillative step. For instance, a solid material can be separated off by filtration, centrifugation, sedimenting, decanting or aspiration. In general, the solid materials obtained are salts $[M^{a+}]X^-_a$, possibly including carboxylic acid salts of general formula II or catalysts. The filter cake, the sediment and the centrifugation pellet are preferably washed, preferably with a high boiler solvent HBS, and the wash liquor is preferably fed together with the product solution into the distillative step. When the solid material contains a catalyst, the solvent selected for washing the filter cake can be for example such that, in a first wash cycle, only the adherent reaction product is washed off as solution and preferably fed to the distillative step, and, in a further wash cycle, a suitable different solvent can be chosen to wash off the catalyst without other salts dissolving to any significant degree, and the catalyst thus washed off can preferably be sent for recycling, optionally after removal of the solvent. Multiple liquid phases can optionally be separated prior to the distillative step. Preferably, the phases with the highest product concentrations are fed to the distillative step. Catalysts can form liquid phases which can also contain solvents, starting materials and products. Whether such catalyst phases are preferably sent to the distilland or preferably directly for recycling, depends on their product content and on whether the catalyst phases interfere in the distillative step, which a person skilled in the art can readily ascertain in preliminary testing.

Solvents can form liquid phases which can also contain catalysts, starting materials and products. Whether such solvent phases are preferably fed to the distilland or preferably sent directly for recycling depends on their product content and on whether the catalyst phases interfere in the distillative step, which a person skilled in the art can easily ascertain by preliminary testing. When the solvent phases are high boiler solvent HBS or consist of HBS to an extent of 50% or more, these phases are preferably fed to the distilland.

One or more stabilizers can be added before, during or after the distillation. Stabilizers are described above, they can also be used in the distillative step.

The distillate, which contains at least one silane of general formula I with or without further compounds, can be redistilled, for example when further purification or separation of various silanes of general formula I from each or one another or from silanes of general formula III is desired. The distillation conditions to be employed preferably, more preferably and even more preferably are the same as described above. When the distillate has two or more phases, for example solvent phases which are not miscible with the silane of general formula I, the distillate can be further worked up for example by phase separation with or without redistillation.

It is preferable for solvents, catalysts and stabilizers to be recovered and recycled, i.e., be reused in the process of the present invention or in some other process. This can take place before or after the distillative step.

Solvents which are lower boiling than the silane of general formula I can be recovered as preliminary fraction; they are generally reusable without further workup.

Solvents that are higher boiling than the silane of general formula I, i.e., HBS's, are obtained as bottom product in the distillative step (or to be more precise, as unvaporized runoff in the case of a thin layer, falling film or short path distillation). They can be reused unchanged or worked up, for example by filtration, sedimentation and aspiration, decanting, distillation, extraction, incipient stripping or drying or a combination thereof. Whether reuse takes place with or without purification step depends on the impurity profile of the solvent. For instance, solvents with a high salt content (generally more than 10% of salt) are, before reuse, preferably filtered or, when HBS is not completely miscible with water, extracted with a solvent of complementary polarity, for example with water (when an apolar solvent was chosen for HBS), with or without addition of further components to improve phase separation for example. When an extraction step is planned, it is preferable to choose HBS to be an incompletely water-miscible, apolar solvent, for example an ether, an ester, a hydrocarbon, a chlorohydrocarbon or a ketone having at least 4 carbon atoms—preferably a hydrocarbon—or mixtures thereof, and it is preferable to use water as extractant. When catalysts form a separate phase from HBS, the catalyst phase is preferably separated off before the extraction step, for example by filtration, sedimentation and aspiration or decanting in the case of solid phases of catalyst and by phase separation for liquid or dissolved catalysts. When HBS stays in the water, it can be removed for example by incipient stripping, azeotroping, adsorption or extraction with an apolar low-boiling solvent (boiling point preferably <150° C., more preferably <120° C. and even more preferably <100° C.) and phase separation, in which case residues of the low-boiling solvent are subsequently easy to remove from the aqueous phase by incipient stripping.

When HBS contains catalysts, these can be preferably recycled together with HBS in the same stream of material. When HBS is filtered before reuse, undissolved catalyst can remain in HBS or in the filter cake, depending on the solubility; filtered-off catalyst can be dissolved out of the filter cake with a suitable solvent and be reused with or without prior removal of the solvent. When HBS is distilled before reuse, catalysts can be removed for example from the bottom product by dissolving out with a suitable solvent or filtration and reused. When catalysts form a separate phase from HBS, the catalyst phase is easy to separate off, for example by filtration, sedimentation and aspiration or decanting in the case of solid phases of catalyst and by phase separation in the case of liquid catalysts. When HBS is extracted before reuse, catalysts can remain in HBS or in the extractant. Catalyst remaining in HBS can be reused together with HBS. Catalyst remaining in the extractant can for example be back-extracted and reused with or without prior removal of the back-extractant, for example by back-extraction with an ether, ester, hydrocarbon, chlorohydrocarbon, ketone or alcohol.

When a salt was used as catalyst, it may have undergone anion or cation exchange reactions in the course of the process in that, for example, an ammonium or phosphonium salt used as phase transfer catalyst can exchange its anions for $X^-$ or for the employed carboxylate anion $R^1$—C(=O)—O$^-$, or a bromide or iodide used as activator can have exchanged its cation for [$M^{a+}$]. As long as the catalysis-relevant ion (the cation in the case of phase transfer catalysts, the anion in the case of activating bromides or iodides) is still present, the catalyst salt will generally be still active and hence will still be usable in the process and in recycling.

All the above symbols in the above formulae each have their meanings independently of each other. Unless otherwise stated, the above % ages are weight percent. Unless stated otherwise, the reported yields in % of theory are based on the amount of silane used. The silicon atom is tetravalent in all formulae. Unless otherwise stated, all pressures are absolute pressures. Unless stated otherwise, the definition of heteroatom comprehends all elements other than carbon and hydrogen.

EXAMPLES

Unless otherwise stated, the operations described are carried out at atmospheric pressure and room temperature (20-25° C.)

Example 1

Synthesis of (caprylatomethyl)trimethoxysilane

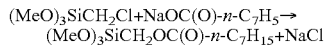

A mixture of 775 mL of bis(2-ethylhexyl) phthalate (=HSB), 11.46 g (33.8 mmol) of tetrabutylphosphonium bromide (=phase transfer catalyst) and 302.6 g (1.82 mol) of sodium caprylate was heated to 120-125° C.

Under agitation, 282.5 g (1.66 mol) of (chloromethyl)-trimethoxysilane were metered in. The mixture was stirred at the same temperature for a further 2 hours. A gas chromatogram (FID detector) showed a peak area ratio of 1:948 for the starting material (chloromethyl)trimethoxysilane to the product (caprylatomethyl)trimethoxysilane (=a silane of general formula I). The product was distilled through a Vigreux column (20 cm) at 1.1-1.3 mbar (head), 122-134° C. (head) and 141-211° C. (pot) to obtain 349 g (1.25 mol, 76% of theory) of the product (caprylatomethyl)trimethoxysilane as a slightly yellowish liquid; purity 86% (GC area %). The solvent, sodium chloride, excess sodium caprylate and the phase transfer catalyst in the form of the chloride, bromide and caprylate salt of tetrabutylphosphonium remain in the residue. The product was redistilled at 1.8-2.2 mbar (head), 129-131° C. (head) and 151-155° C. (residue) through a packed column (20 cm); a slight yellow hue remained in the product after redistillation; purity 93.2% (GC area %).

Example 2

Synthesis of (acetoxymethyl)trimethoxysilane

A mixture of 179 L of Hydroseal G 400 H(=HBS, said by the manufacturer Total to be a $C_{17}$-$C_{21}$ hydrocarbon mixture having a density of 815 kg/m$^3$, a boiling range of 304-349° C. and an aromatics content of 0.01%) and 100 kg (1.22 kmol) of sodium acetate was heated up for one hour at 150° C./1 mbar (for drying). The heating was switched off, the vacuum was broken with nitrogen and 7.51 kg (22.2 mol) of tetrabutylphosphonium bromide (=phase transfer catalyst) were added and the temperature was adjusted to 120° C. Under agitation, 189.2 kg (1.11 kmol) of (chloromethyl)trimethoxysilane were metered in over 2.5 hours. The mixture was stirred at the same temperature for a further 4 hours. A cooled sample separated into 3 phases (1 solid, 2 liquid). The solid phase contained mainly sodium chloride and sodium acetate, the bottom liquid phase contained mainly (acetoxymethyl)trimethoxysilane (=a silane of formula I) and the phase transfer catalyst in the form of the chloride, bromide and acetate salt of tetrabutylphosphonium, and the top phase contained mainly the solvent and low concentrations of (acetoxymethyl)trimethoxysilane. A gas chromatogram (FID detector) of the silane phase showed a peak area ratio of 1:5605 for the starting material (chloromethyl)trimethoxysilane to the product (acetoxymethyl)trimethoxysilane. The product was distilled through a sieve plate column; a very pure middle cut was obtained at 10 mbar (head), 60-61° C. (head) and 89-125° C. (pot) (171.1 kg, purity 99.6%). The preliminary cut (10 mbar (head), 26-60° C. (head), 89-94° C. (pot); 5.3 kg, purity 94.9%) and the after-cut (10→1 mbar (head), 61→40° C. (head), 125-160° C. (pot); 26.7 kg, purity 98.1%) were combined and redistilled (redistillation: sieve plate column, 24 mbar (head), 79-81° C. (head), 100-110° C. (pot)), to obtain a further 31.0 kg of the product (purity 99.1%); purities in GC area %. This gave a total of 202.1 kg (1.04 kmol, 94% of theory) of the product (acetoxymethyl)trimethoxysilane as colorless liquid. The solvent, sodium chloride, excess sodium acetate and the phase transfer catalyst in the form of the chloride, bromide and acetate salt of tetrabutylphosphonium remained in the residue.

Example 3

Synthesis of (acetoxymethyl)trimethoxysilane

(MeO)$_3$SiCH$_2$Cl+NaOC(O)Me→(MeO)$_2$SiCH$_2$OC(O)Me+NaCl

Example 2 was repeated using sodium acetate (312 g, 3.81 mol) and (chloromethyl)trimethoxysilane (563 g, 3.30 mol) as starting materials, tetrabutylphosphonium bromide (22.46 g, 66.2 mmol) as catalyst and methyl laurate (525 mL) as solvent. Before the silane was added, the other components were mixed and incipiently stripped at 116° C./4 mbar (for drying, 16 g of distillate). The silane was metered in at 120° C. over 2 hours, the mixture was heated at 120° C. for a further 4 hours and then distilled at 10-11 mbar (head), 74-76° C. (head) and 88-122° C. (pot) through a packed column (20 cm) to obtain 608 g (3.13 mol, 95% of theory) of (acetoxymethyl)trimethoxysilane in the distillate; purity 98.6% (GC area %). The solvent then started to pass over at 3.1 mbar (head), 113° C. (head) and 128° C. (pot). By distilling over a small amount (about 10 g) of the solvent, the product (acetoxymethyl)trimethoxysilane was fully removed from the residue. The remaining solvent, sodium chloride, excess sodium acetate and the phase transfer catalyst (in the form of the bromide, chloride and acetate salt of tetrabutylphosphonium) remained in the residue.

Example 4

Synthesis of (acetoxymethyl)dimethoxymethylsilane

(MeO)$_2$MeSiCH$_2$Cl+KOC(O)Me→(MeO)$_2$MeSiCH$_2$OC(O)Me+KCl

Example 2 was repeated using potassium acetate (405 g, 4.13 mol) and (chloromethyl)dimethoxymethylsilane (535 g, 3.46 mol) as starting materials, tetrabutylphosphonium bromide (35.0 g, 10.3 mmol) as catalyst and diethylene glycol dibutyl ether (525 mL) as solvent. After the reaction, the product was distilled at 10 mbar (head), 61-70° C. (head) and 80-119° C. (pot) through a packed column (20 cm) to obtain 560 g (3.14 mol, 91% of theory) of (acetoxymethyl)dimethoxymethylsilane in the distillate; purity 98.0% (GC area %). The solvent then started to pass over at 10 mbar (head), 118° C. (head) and 124° C. (pot); by distilling over about 10 g of solvent, the (acetoxymethyl)dimethoxymethylsilane was fully removed from the residue. The solvent, potassium chloride, excess potassium acetate and the phase transfer catalyst (in the form of the bromide, chloride and acetate salt of tetrabutylphosphonium) remained in the residue.

Example 5

Synthesis of (acetoxymethyl)dimethoxymethylsilane, Aqueous Workup of Distillation Residue and Reuse (Recycling) of Catalyst and High Boiler Solvent (MeO)$_2$MeSiCH$_2$Cl+NaOC(O)Me→(MeO)$_2$MeSiCH$_2$OC)Me+NaCl Example 5a Reaction and Workup A mixture of 10.7 L of Hydroseal G 400 H(=HSB, $C_{17}$-$C_{21}$ hydrocarbon mixture, see above) and 5.97 kg (72.8 mol) of sodium acetate was heated up for one hour at 150° C./2 mbar (for drying). The heating was switched off, the vacuum was broken with nitrogen and 450 g (1.32 mol) of tetrabutylphosphonium bromide (=phase transfer catalyst) were added and the temperature was adjusted to 120° C. Under agitation, 10.24 kg (66.2 mol) of (chloromethyl)dimethoxymethylsilane (=a silane of formula II) were metered in over 2 hours. The mixture was stirred at the same temperature for a further 3 hours. The product was distilled out through a sieve plate column; the product (acetoxymethyl)dimethoxymethylsilane was obtained at 53-54 mbar (head), 70-73° C. (head) and 100-125° C. (pot) in the distillate (10.8 kg, 60.6 mol, 92% of theory; purity 99.5% (GC area %)) as a colorless liquid. The solvent, sodium chloride, excess sodium acetate and the phase transfer catalyst in the form of the chloride, bromide and acetate salt of tetrabutylphosphonium remained in the residue (18.5 kg in total).

Example 5b

Recovery of Solvent and Catalyst

A sample was taken of the distillation residue in Example 5a under agitation such that the 963 g (1042 mL) sample contained representative aliquots of liquid and solid. The still hot sample (80° C.) was admixed under agitation with just sufficient water to dissolve the salt (633 mL of water at 19° C.)

Thereafter, the temperature of the mixture was 44° C. Left to stand, the mixture was observed to speedily separate into three clear, liquid phases: at the top, a Hydroseal-rich phase (880 mL, 857 g), yellow; in the middle, a catalyst-rich phase (catalyst in the form of the chloride, bromide and acetate salt of tetrabutylphosphonium; 60 mL, 95.4 g), dark brown; at the bottom, an aqueous phase with dissolved sodium salts (chloride, bromide, acetate), yellow. Inductively coupled plasma/optical emission spectroscopy (ICP-OES; analyzed element: phosphorus) was used to determine that, of the phase transfer catalyst originally used, 4% were in the Hydroseal phase, 18% in the aqueous phase and the remainder in the middle phase, calculated on the amount of substance of tetrabutylphosphonium ions in the aliquot taken. Nuclear magnetic resonance (nucleus: $^{31}$P, 202.5 MHz, δ=33.4 ppm, solvent $d_6$-acetone) of the middle phase confirmed that the catalyst post-reaction was still in the form of the tetrabutylphosphonium salts.

A 300 mL quantity of n-butanol was added and the mixture was stirred. After standing and phase separation, ICP-OES for phosphorus showed that 14% of the catalyst originally used was in the top, Hydroseal phase (919 mL, 733 g), 0.4% in the bottom aqueous phase (720 mL, 856 g) and the remainder in the middle, catalyst phase (200 mL, 175 g). The n-butanol was mainly in the catalyst phase; 6.8 g were in the aqueous phase and 0.5 g in the Hydroseal phase ($^1$H NMR check, internal standard: naphthalene ($C_6D_6$, top, Hydroseal phase; $d_6$-acetone, middle, catalyst phase) or sodium 3-trimethylsilyl-2,2,3,3-d-4-propionate ($D_2O$, bottom, aqueous phase)).

The aqueous phase was separated off and the n-butanol was distillatively removed from the aqueous phase by distilling off $\frac{1}{10}$ of the aqueous phase at 350 mbar (head), 66-73° C. (head) and 75-80° C. (pot) to obtain a biphasic distillate consisting in the main of n-butanol and water; this azeotropic distillation gave an aqueous phase which was butanol and hydrocarbon free within the limits of detection ($^1$H NMR check, $D_2O$).

The top, Hydroseal phase and the middle, catalyst phase were combined and n-butanol therein was removed by distillation (300→20 mbar (head), to 75° C. (head) or to 95° C. (pot)). Of the remaining mixture, a small amount of solvent (about 10 mL of Hydroseal G 400 H) was distilled off through a Vigreux column (80 cm) at 1-2 mbar (head), 120-135° C. (head), 150-160° C. (pot) for drying.

Example 5c

Recovery of Solvent and Catalyst

Example 5b was repeated except that only 150 mL of n-butanol were used. Thereafter, the aqueous phase contained 0.3% and the Hydroseal phase 12% of the catalyst originally used, based on the employed aliquot of the residue from Example 5a. The rest of the workup was accomplished similarly to Example 5b.

Example 5d

Recovery of Solvent and Catalyst

Example 5b was repeated, except that directly following the aqueous workup the aqueous phase was separated from the other phases before the extraction with n-butanol was carried out. Solely the aqueous phase was extracted with n-butanol; after extraction, the aqueous phase still contained 0.4% of the catalyst originally used, based on the employed aliquot of the residue from Example 5a. The n-butanol contained the catalyst extracted from the aqueous phase. The rest of the workup of the extracted aqueous phase was accomplished similarly to Example 5b. The Hydroseal and catalyst phases were combined with the (catalyst-containing) n-butanol phase from the extraction; workup and reuse were accomplished similarly to Example 5e (see hereinbelow). Optionally, the distillative removal of n-butanol and water from the Hydroseal and catalyst phases in the recycling step was also carried out after (instead of before, cf. Example 5e) addition of sodium acetate.

Examples 5b, c and d show how a product of the process according to the present invention can be worked up without a single time-consuming filtration step; how solvent and catalyst can be recovered by aqueous workup; and how the resulting aqueous phase can be freed of catalyst and of solvents, making it possible for the salt load to be sent for disposal in the form of the worked-up aqueous phase.

Example 5e

Reuse (Recycling) of Solvent and Catalyst

The top, Hydroseal phase and the middle, catalyst phase from Example 5b were admixed with 180 g (2.2 mol) of sodium acetate and the suspension was dried by distilling 10 mL of Hydroseal G 400 H off through a Vigreux column (80 cm) at 1-2 mbar (head), 120-135° C. (head), 150-160° C. (pot). The suspension was cooled down to 130° C., at which point 308 g (2.00 mol) of (chloromethyl)dimethoxymethylsilane were metered in over 47 minutes. The product was distilled out through a Vigreux column (80 cm); the product (acetoxymethyl)dimethoxymethylsilane was obtained at 30 mbar (head), 71-73° C. (head) and 73-80° C. (pot) in the distillate (334 g, 1.87 mol, 94% of theory; purity 99.1% (GC area %)) as a colorless liquid. The solvent, sodium chloride, excess sodium acetate and the phase transfer catalyst in the form of the chloride, bromide and acetate salt of tetrabutylphosphonium remained in the residue.

Example 5e shows that recovered solvent and catalyst can be reused in the process of the present invention.

Example 6

Synthesis of (formoxymethyl)trimethoxysilane

$(MeO)_3SiCH_2Cl+NaOC(O)H→(MeO)_3SiCH_2OC(O)H+NaCl$

A mixture of sodium formate (53.6 g, 788 mmol) and high boiler solvent dimethylpropyleneurea (DMPU, 1,3-dimethyl-3,4,5,6-tetrahydro-2(1H)-pyrimidinone) (400 mL) was admixed with 100 mL of toluene. To dry the mixture, the toluene was distilled off (47 mbar (head), 26-29° C. (head), 68-90° C. (pot)) and then the vacuum was tightened until only DMPU passed over (1.2 mbar (head), 89° C. (head), 110° C. (pot); about 10 g of DMPU distillate). The remaining mixture was cooled down to 100° C., and (chloromethyl)trimethoxysilane (128 g, 750 mmol) was metered in over 5 minutes, and the resulting mixture was stirred at 100° C. for 30 minutes and at 115° C. for a further 2.5 hours. A reaction check showed complete conversion of the (chloromethyl)trimethoxysilane, and also the desired product (formoxymethyl)trimethoxysilane and the by-products methyl formate, tetramethoxysilane and siloxanes of the silanes formed. The product was distilled at 100° C. temperature (pot) by gradually tightening the vacuum from 15 mbar to 3 mbar (boiling point 59-91° C.

(head)). The distillate obtained contained 66.9 g of (formoxymethyl)trimethoxysilane (purity 73.6% (GC area %)); the distillate contained, based on purity, 61.7 g (342 mmol, 46% of theory) of (formoxymethyl)-trimethoxysilane. The solvent, sodium chloride and excess sodium formate remained in the residue.

Example 7

Synthesis of (formoxymethyl)methoxydimethylsilane

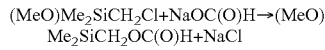

(MeO)Me$_2$SiCH$_2$Cl+NaOC(O)H→(MeO)Me$_2$SiCH$_2$OC(O)H+NaCl

A mixture of sodium formate (5.00 kg, 73.5 mol) and Hydroseal G 400 H (14.9 L) was heated to 150° C. at 1 mbar for one hour (for drying). The vacuum was broken with nitrogen and the mixture was cooled down to 120° C., at which point tetrabutylphosphonium bromide (450 g, 1.34 mol) was added as catalyst. (Chloromethyl)methoxydimethylsilane (9.27 kg, 66.8 mol) was metered in over 2 hours and the resulting mixture was stirred at 120° C. for 3 hours. A gas chromatogram (FID detector) showed a peak area ratio of 1:274 for the starting material (chloromethyl)methoxydimethylsilane to the product (formoxymethyl)methoxydimethylsilane. The product was distilled at 155 mbar (head), 73-76° C. (head) and 100-151° C. (pot). The solvent, sodium chloride, excess sodium formate and the phase transfer catalyst (in the form of the bromide, chloride and formate salt of tetrabutylphosphonium) remained in the residue. The distillate obtained contained 9.41 kg of (formoxymethyl)methoxydimethylsilane in a purity of 99.1%, which still contained 0.5% of (chloromethyl)-methoxydimethylsilane; the latter has a lower boiling point than the product and was separated off by distilling 745 g of the product off through a sieve plate column (198 mbar (head), 87° C. (head), 99° C. (pot), leaving (formoxymethyl)methoxydimethylsilane in 99.7% purity in the pot (purities in GC area %).

Example 8

Synthesis of (crotonatomethyl)trimethoxysilane (cis/trans mixture)

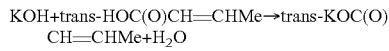

KOH+trans-HOC(O)CH=CHMe→trans-KOC(O)CH=CHMe+H$_2$O

Crotonic acid (75.0 kg, 871 mol) was suspended in 90 L of water in a stirred tank. A 53% aqueous potassium hydroxide solution was metered in over an hour until a pH of 7.1 was obtained. In the process, the temperature rose from 20° C. to 52° C. The mixture was stirred for a further hour (pH: 7.25). The bulk of the water was distilled off at 190→130 mbar and 65→60° C. (pot). The residue was then transferred into a conical dryer, the remaining water was distilled off at 160→130 mbar and 65→60° C. (pot) to obtain 53.3 kg of distillate. In the course of water being distilled off, 777 g of crotonic acid (1% of amount used) passed over with the water (quantitative HPLC check of distilled-off water). The residue was dried by heating with 0.5 bar relative (1.5 bar absolute) superheated steam (about 106° C.) and 9-15 mbar for one hour and then with 1.5 bar relative (2.5 bar absolute) superheated steam (about 120° C.) and 3-4 mbar for a further three hours. The product potassium crotonate was obtained in 99% yield in the form of colorless finely crystalline platelets and was shown by HPLC to be isomerically pure (trans); the pH of a sample (1 g) dissolved in water (10 mL) was 7-7.5 (Neutralit indicator paper). Solvent: High-Boiling Fraction of Hydroseal G 400 H Hydroseal G 400 H (hydrocarbon mixture, see above) was partially fractionated in vacuo. About 30% of the solvent was distilled off in vacuo at 3 mbar (head), 19-23 mbar (pot), 120-130° C. (head) and 175-206° C. (pot). The higher-boiling residue of the distillation was used in the next step.

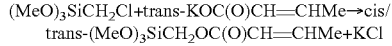

(MeO)$_3$SiCH$_2$Cl+trans-KOC(O)CH=CHMe→cis/trans-(MeO)$_3$SiCH$_2$OC(O)CH=CHMe+KCl A mixture of trans-potassium crotonate (4.97 kg, 40.0 mol), phenothiazine (stabilizer, 3.99 g, 20.0 mmol), tetrabutylphosphonium bromide (270 g, 79.6 mmol) and the high-boiling fraction of Hydroseal G 400 H (distillation residue from the preceding step, 13.2 L) was heated to 120° C. at 3 mbar for one hour (for drying). The vacuum was broken with nitrogen and the mixture was heated up to 130° C., at which point (chloromethyl)trimethoxysilane (6.83 kg, 40.0 mol) was metered in over 1¾ hours. The mixture was stirred at 130° C. for a further 4 hours, at which point 2,6-di-tert-butyl-4-methylphenol (BHT, stabilizer, 4.41 g, 20.0 mmol) was added. The product was distilled out at 1-3 mbar (head), 71-73° C. (head) and 108-158° C. (pot) to obtain the product (crotonatomethyl)trimethoxysilane (7.53 kg, 34.2 mol, 85% of theory) in the distillate in the form of the cis/trans mixture (82.6% cis, 13.5% trans); the product further contained 3.1% of the constitutional isomer (but-3-enoatomethyl)trimethoxysilane; purity 99.2% (sum total of cis, trans and but-3-enoato isomers); the distillate additionally contained 0.13% of (chloromethyl)trimethoxysilane (content/purity data in GC area %). The solvent, potassium chloride, traces of unconverted potassium crotonate and the phase transfer catalyst (in the form of the bromide, chloride and crotonate salt of tetrabutylphosphonium) remained in the residue. The (chloromethyl)trimethoxysilane was separated off by distilling 5% of the product off at 2 mbar (head), 57-71° C. (head) and 93-97° C. (pot), which caused the (chloromethyl)trimethoxysilane to pass over and left the largest part of the reaction product behind in the residue.

Example 9

Synthesis of (acetoxymethyl)methoxydimethylsilane

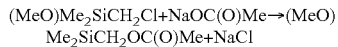

(MeO)Me$_2$SiCH$_2$Cl+NaOC(O)Me→(MeO)Me$_2$SiCH$_2$OC(O)Me+NaCl

A mixture of 20 mL of high boiler solvent as per Table 1, 13.5 g (165 mmol) of sodium acetate (anhydrous) and the Table 1 amount of phase transfer catalyst (amount specified in mol % based on employed amount of silane) was heated to the temperature reported in Table 1 and dried at this temperature under a vacuum of 10 mbar for minutes. The vacuum was subsequently broken with argon, and (chloromethyl)methoxydimethylsilane (20.8 g, 150 mmol) was metered in at this temperature over 30 minutes under agitation. The mixture was further stirred at this temperature until a gas chromatogram (FID detector) or a $^1$H NMR spectrum indicated more than 99% conversion of the silane; the reaction times required for this are reported in Table 1. The product was subsequently distilled off at 10-90 mbar (head), 50-90° C. (head) and 70-120° C. (pot) through a Widmer column (20 cm) to obtain the Table 1 yields of (acetoxymethyl)methoxydimethylsilane as a colorless liquid having a purity of >99% (GC area %). The solvent, sodium chloride, excess sodium acetate and the phase transfer catalyst in the form of its chloride and acetate salts (and also of the bromide salt when a bromide was used) remained in the residue.

TABLE 1

| No. | Solvent | Catalyst | T/°C. | t/h | Yield |
|---|---|---|---|---|---|
| a | Hydroseal G 400 H | 2 mol % of $Bu_4PCl$ | 120 | 3 | 19.1 g/ 79% |
| b | Hydroseal G 400 H | 2 mol % of Cyphos ®IL101 $[(H_{13}C_6)_3(H_{29}C_{14})P]Cl$ | 120 | 2 | 18.8 g/ 77% |
| c | Hydroseal G 400 H | 2 mol % of Aliquat ® 336 $[Me(H_{17-21}C_{8-10})_3N]Cl$ | 90 | 9 | 22.4 g/ 92% |
| d | Hydroseal G 400 H | 2 mol % of Arquad ® 2HT-75 $[Me_2(H_{33-37}C_{16-18})_2N]Cl$ | 120 | 7 | 17.8 g/ 72% |
| e | Hydroseal G 400 H | 2 mol % of Präpagen ® WK $[Me_2(H_{33-37}C_{16-18})_2N]Cl$ | 120 | 11 | 16.6 g/ 68% |
| f | Hydroseal G 400 H | 2.5 mol % of hexaethyl-guanidinium chloride | 120 | 1 | 22.4 g/ 92% |
| g | Hydroseal G 400 H | 0.5 mol % of hexaethyl-guanidinium chloride | 120 | 3 | 22.3 g/ 91% |
| h | PPG 2000 | 2 mol % of $Bu_4PBr$ | 120 | 4 | 16.2 g/ 67% |
| i | tributyl phosphate | 2 mol % of $Bu_4PBr$ | 120 | 2 | 14.4 g/ 59% |
| j | diphenyl ether | 2 mol % of $Bu_4PBr$ | 120 | 3 | 18.9 g/ 78% |
| k | dibenzyl ether | 2 mol % of $Bu_4PBr$ | 120 | 4.5 | 17.5 g/ 72% |
| l | Marlotherm SH (dibenzyl-toluene) | 2 mol % of $Bu_4PBr$ | 120 | 5 | 19.9 g/ 82% |
| m | Tributyrin (glycerol tributyrate) | 2 mol % of $Bu_4PBr$ | 120 | 3 | 19.2 g/ 79% |
| n | Plaxolene 25 | 2 mol % of $Bu_4PBr$ | 120 | 5 | 18.0 g/ 74% |

Example 10

Synthesis of (acetoxymethyl)methoxydimethylsilane, workup of distillation residue by filtration

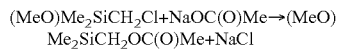
$(MeO)Me_2SiCH_2Cl+NaOC(O)Me \rightarrow (MeO)Me_2SiCH_2OC(O)Me+NaCl$ A mixture of 61.1 kg of Hydroseal G 400 H and 50 kg (609.4 mol) of sodium acetate was dried by heating at 150° C./2 mbar for 1.5 h. After cooling down to below 120° C., the vacuum was broken with nitrogen, 3.76 kg (11.1 mol) of tetrabutylphosphonium bromide were added and the temperature was adjusted to 120° C. Then, under agitation, 73.2 kg (528 mol) of (chloromethyl)methoxydimethylsilane were metered in over 2.5 h. The mixture was subsequently stirred at the same temperature for a further 4 h. The product was then distilled out through a column at 20 mbar (head), 46-55° C. (head) and 73-145° C. (pot), while a further 36.7 kg of Hydroseal G 400 H were metered in during the distillation to ensure stirrability. The product (acetoxymethyl)methoxydimethylsilane (80.4 kg, 495.5 mol, 94% of theory; purity 99.4% (GC area %)) was obtained as a colorless liquid. The solvent, sodium chloride, excess sodium acetate and the phase transfer catalyst in the form of the chloride, bromide and acetate salt of tetrabutylphosphonium remained in the residue. The residue was worked up by filtration using an inverting filter centrifuge to give 93 kg of filtrate (Hydroseal) and 41 kg of solid material (NaCl, NaOAc, $Bu_4PBr$; anions and cations exchanged in part). The filter cake was washed with xylene (isomer mixture, 2×20 L) and filtered once more by the same method. The filtrate contained the xylene-soluble phase transfer catalyst in the form of the chloride, bromide and acetate salt of tetrabutylphosphonium, the filter cake contained above all the sodium salts of the chloride, in part also of the acetate and of the bromide. The solvent thus recovered and the recovered catalyst can be reused, in which case the xylene can optionally be distilled off or co-used.

Example 11

Synthesis of (acetoxymethyl)methoxydimethylsilane, Workup of Distillation Residue by Hydrolysis

$(MeO)Me_2SiCH_2C+NaOC(O)Me \rightarrow (MeO)Me_2SiCH_2OC(O)Me+NaCl$

Example 11a

Reaction and Workup

A mixture of 61.1 kg of Hydroseal G 400 H and 50 kg (609.4 mol) of sodium acetate was dried by heating at 150° C./2 mbar for 1 h. After cooling down to 112° C., the vacuum was broken with nitrogen, 3.76 kg (11.1 mol) of tetrabutylphosphonium bromide were added and the temperature was adjusted to 120° C. Then, under agitation, 76.8 kg (554 mol) of (chloromethyl)methoxydimethylsilane were metered in over 1 h. The mixture was subsequently stirred at the same temperature for a further 6 h. The product was then distilled out through a column at 20 mbar (head), 50-56° C. (head) and 70-145° C. (pot), while a further 36.7 kg of Hydroseal G 400 H were metered in during the distillation to ensure stirrability. The product (acetoxymethyl)methoxydimethylsilane (89.0 kg, 548.5 mol, 99% of theory; purity 99.5% (GC area %)) was obtained as a colorless liquid. The solvent, sodium chloride, excess sodium acetate and the phase transfer catalyst in the form of the chloride, bromide and acetate salt of tetrabutylphosphonium remained in the residue.

Example 11b

Recovery of Solvent and Catalyst

After cooling down to 80° C., the distillation residue was admixed under agitation with just sufficient water to dissolve the salt (100 liters). On standing and separation of the mixture, three clear, liquid phases were observed: at the top, a Hydroseal-rich phase (100 kg), yellow; in the middle, a catalyst-rich phase (catalyst in the form of the chloride, bromide and acetate salt of tetrabutylphosphonium; 4 kg), dark brown; at the bottom, an aqueous phase with dissolved sodium salts (chloride, bromide, acetate; 134 kg), yellow. The aqueous phase was separated off, mixed with 25 l of n-butanol and stirred for one hour. After phase separation, n-butanol in the aqueous phase was removed by distilling 1/10 of the aqueous phase off at 98-105° C. (pot) at atmospheric pressure (around 1 bar absolute) to obtain a 2-phasic distillate consisting in the main of n-butanol and water. Azeotropic distillation gave an aqueous phase which is butanol and hydrocarbon free within the limits of detection ($^1$H NMR, $D_2O$).

Example 11c

Reuse (Recycling) of Solvent and Catalyst

Solvent and catalyst recovered as per Example 11b were reusable for preparing (acetoxymethyl)methoxydimethylsilane by combining the methods of Example 5a (removing the n-butanol from the Hydroseal phase and from the catalyst phase), Example 5e (drying) and Example 11a (reaction).

Example 11 shows how a product of the process according to the present invention can be worked up without a single time-consuming filtration step; how solvent and catalyst can be recovered by aqueous workup; and how the resulting aqueous phase can be freed of catalyst and of solvents, making it possible for the salt load to be sent for disposal in the form of the worked-up aqueous phase.

Example 12

Synthesis of (acetoxymethyl)methoxydimethylsilane, solvent Only Added During the Distillation (MeO)Me$_2$SiCH$_2$Cl+NaOC(O)Me→(MeO)Me$_2$SiCH$_2$OC(O)Me+NaCl A mixture of 230.4 kg (1.662 kmol) of (chloromethyl)methoxydimethylsilane and 11.8 kg (34.8 mol) of tetrabutylphosphonium bromide was heated up to 90° C. and admixed during 3 h with 150 kg (1.828 kmol) of sodium acetate (anhydrous) in 6 portions of 25 kg each such that the temperature did not exceed 114° C. The mixture was subsequently stirred without additional heating for 1 h and then at 115-122° C. for a further 2 h. Thereafter, the product was distilled out through a column at 18-30 mbar (head), 50-53° C. (head) and 84-120° C. (pot), while 150 kg of Hydroseal G 400 H were metered into the residue during the distillation to ensure stirrability. The product (acetoxymethyl)methoxydimethylsilane (249.2 kg, 1.536 kmol, 92% of theory; purity 99.6% (GC area %)) was obtained as a colorless liquid. The solvent, sodium chloride, excess sodium acetate and the phase transfer catalyst in the form of the chloride, bromide and acetate salt of tetrabutylphosphonium remained in the residue.

The invention claimed is:

1. A process for producing silanes of formula I $$R^1\text{---}C(\!=\!O)\text{---}O\text{---}R^2\text{---}SiR^3{}_3 \tag{I}$$

comprising reacting at least one salt of a carboxylic acid of formula II $$[R^1\text{---}C(\!=\!O)\text{---}O]_a[M^{a+}] \tag{II}$$

with at least one silane of formula III $$X\text{---}R^2\text{---}SiR^3{}_3 \tag{III}$$

to form a product mixture, and distilling the product mixture to provide a distillate containing at least one silane of formula I, wherein at least one high-boiling solvent HBS is present in the product mixture during at least a portion of said distilling,
wherein the HBS has a higher boiling point than the silane of formula I when measured at the pressure at which distilling is carried out, wherein X is a leaving group which is carboxylate substitutable, $R^1$ is hydrogen or a monovalent $C_1$-$C_{18}$ hydrocarbon radical which is unsubstituted or substituted with one or more groups Q, optionally interrupted by one or more heteroatoms, Q when attached to an sp$^3$-hybridized carbon atom is a hydrocarbonoxy, acyloxy, hydrocarboncarbonyl, carbonyl, hydrocarbonoxoy-carbonyl, hydrocarbonsulfide, acylsulfide, cyano or nitro group, and when attached to an sp$^2$- or to an sp-hybridized carbon atom, is a hydrocarbonoxy, acyloxy, hydrocarboncarbonyl, carbonyl, hydrocarbonoxycarbonyl, hydrocarbonsulfide, acylsulfide, cyano or nitro group or has the meaning of X, $R^2$ is a divalent $C_1$-$C_{18}$ hydrocarbon group which is unsubstituted or substituted with one or more groups Q, and is optionally interrupted by one or more heteroatoms, $R^3$ is hydrogen, or an unsubstituted or Q-mono- or -polysubstituted monovalent $C_1$-$C_{18}$ hydrocarbon group, $C_1$-$C_{18}$ hydrocarbonoxy group, $Si_1$-$Si_4$ silane group or an $Si_1$-$Si_4$ siloxy group which is optionally interrupted by one or more heteroatoms, $M^{a+}$ is an a-tuply positively charged cation, and a is an integer not less than 1.

2. The process of claim 1, wherein $R^2$ is selected from —CH$_2$— or —CH$_2$CH$_2$CH$_2$—.

3. The process of claim 1, further comprising directly distilling the product mixture obtained by reacting the carboxylic acid salt of formula II with the silane of formula III without a prior filtration step.

4. The process of claim 1, wherein the product mixture from the reaction of the carboxylic acid salt of formula II with the silane of formula III is distilled directly, without further intervening steps.

5. The process of claim 1, which takes place in the presence of a catalyst.

6. The process of claim 5, wherein the catalyst is a phase transfer catalyst.

7. The process of claim 5, wherein the catalyst is a salt of a bromide or iodide which activates the group X—$R^2$ in the silane of formula III by substitution of X by bromide or iodide.

8. The process of claim 1, wherein less than 80% of solvents used in the process have a boiling point in the distillative step which is equal to or below that of the silane of formula I, calculated in weight % based on the sum total of all solvents used in the process, wherein the boiling points are measured at the pressure at which distilling takes place.

9. The process of claim 1, wherein the proportion of solvents which meet the boiling point criteria for HBS is at least 20%, based in weight % on the sum total of all solvents used in the process.

10. The process of claim 8, wherein no solvent with a boiling point equal to or below that of the silane of formula I is used.

11. The process of claim 9, wherein no solvent with a boiling point equal to or below that of the silane of formula I is used.

* * * * *